United States Patent [19]

Dodd

[11] 4,449,255
[45] May 22, 1984

[54] EYEPIECE FOR PROTECTIVE DEVICES

[75] Inventor: Frederick H. Dodd, Porton near Salisbury, England

[73] Assignee: The Secretary of State for Defence in Her Britannic Majesty's Government of the United Kingdom of Great Britain and Northern Ireland, London, England

[21] Appl. No.: 241,220

[22] Filed: Mar. 6, 1981

[30] Foreign Application Priority Data

Mar. 11, 1980 [GB] United Kingdom ............... 8008228

[51] Int. Cl.³ .............................................. A61F 9/04
[52] U.S. Cl. ...................................................... 2/428
[58] Field of Search ..................... 2/428, 429, 430, 68, 2/431, 439, 440; 128/206.23

[56] References Cited

U.S. PATENT DOCUMENTS

| 1,483,226 | 2/1924 | Johnson | 2/68 |
| 2,737,659 | 3/1956 | Glidden | 2/428 |
| 4,279,039 | 7/1981 | Drew | 2/428 |

FOREIGN PATENT DOCUMENTS

| 0184252 | 5/1907 | Fed. Rep. of Germany | 128/206.23 |
| 0101104 | 3/1941 | Sweden | 2/424 |
| 0108817 | 10/1943 | Sweden | 128/206.23 |

Primary Examiner—Peter P. Nerbun
Attorney, Agent, or Firm—Stevens, Davis, Miller & Mosher

[57] ABSTRACT

A unitary transparent eyepiece has a planar outer rim and a planar inner viewing zone, the plane of the inner viewing zone being inclined at an angle to the plane of the outer rim.

The angle between the, preferably circular, inner viewing zone and the, preferably circular, outer rim of the eyepiece is chosed such that when the planar outer rim is fitted into the planar socket of a face-piece in a protective device, the inner viewing zone is orthogonal to the line of forward vision of the wearer. In this way the face piece conforms to the shape of the wearer's head, an efficient planar and circular seal is obtained between the eyepiece and its socket, and optical aberrations (associated with curved eyepieces) are minimized.

The position of the inner viewing zone relative to the outer rim may be varied according to the clearance required between the eyepiece and the wearer's eye and the type of face piece employed. Certain eyepieces of this design are reversible and may be used in both the right hand and left hand sockets of a face-piece.

3 Claims, 4 Drawing Figures

EYEPIECE FOR PROTECTIVE DEVICES

The present invention relates to a unitary transparent eyepiece for goggles, respirators and the like.

It is a preferred feature of many goggles, respirators and similar protective devices that their shape conforms closely to the shape of the human head. Most of said protective devices comprise a rigid frame, provided with a face-piece and either a unitary curved transparent visor or two, spaced-apart, curved, transparent eyepieces, which also substantially conform to the shape of the human head and, in addition, afford the wearer the maximum width of vision.

There are a number of disadvantages associated with the use of such curved visors and eyepieces. First, in order to accommodate the curved visor or eyepiece in the protective device it must be set in a curved socket, leading to greater difficulties in obtaining a firm, and especially gas-tight, seal than would be experienced between their planar counterparts.

Second, a curved visor or eyepiece will generally be non-orthogonal to the line of forward vision of the wearer and this can often lead to optical aberrations, especially when the wearer of the protective device wishes to employ an optical instrument such as a pair of binoculars or a microscope.

It is an object of the present invention to provide an eyepiece that solves the problems of curved visors or eyepieces whilst still being able to be set in a face piece that generally follows the shape of the human head.

According to the present invention there is provided a unitary transparent eyepiece comprising a planar outer rim and a planar inner viewing zone, wherein the plane of said inner viewing zone is inclined at an angle to the plane of said outer rim.

The angle at which the inner viewing zone is included to the plane of the outer rim will depend on the shape of the face-piece of the protecting device and in particular the angle at which the planar socket into which the eyepiece is to be set is inclined to the line of forward vision of the wearer. Thus the angle between the inner zone and outer rim of the eyepiece is chosen such that the planar outer rim is fitted into the planar socket of the face-piece, the inner viewing zone of the eyepiece is orthogonal to the line of forward vision of the wearer.

In this way two of the disadvantages associated with curved visors or eyepieces are overcome. First the seal between the eyepiece and its socket will be planar, affording the firmest, most efficient type of seal. Second the orthogonal arrangement between the inner viewing zone of the eyepiece and the line of forward vision of the wearer of the protective device minimises the optical aberrations experienced by the wearer, especially when said wearer is employing optical instruments such as a pair of binoculars or a microscope.

In a preferred embodiment of the eyepiece of this invention the outer rim of the eyepiece has a circular circumferential outer edge which fits into a circular, planar socket. The major advantage of such a circular design is again that it optimises the firmness of the seal between the socket and the eyepiece. The sealing pressures associated with a circular seal are generally spread around the whole seal, whilst the sealing pressures associated with a non-circular seal vary from point to point around the seal, being higher than average in some positions and lower than average in others. Thus for security of sealing a circular arrangement is preferred. Further the use of a circular eyepiece and frame simplifies the manufacture of the eyepiece and the face-piece of the protective device.

Although the outer edge of the eyepiece is preferably circular the shape of the outer rim of the eyepiece may be annular or non-annular depending on the shape of the inner viewing zone. Again in order to facilitate the manufacture of the eyepiece it is preferred to have a circular inner viewing zone and an annular outer rim.

The position of the inner viewing zone of this eyepiece with respect to the plane of the outer rim is governed in particular by the clearance required between the eyepiece and the eye of the wearer, and on the type of facepiece employed in the protective device. Thus the whole of the inner viewing zone may be, for example, in front of or behind the plane of the outer rim, or the inner viewing zone may be arranged in a position between these two extremes. For example, one half of the inner viewing zone may be in front of the plane of the outer rim whilst the other half is behind said plane.

One particularly advantageous aspect of a preferred circular eyepiece of this invention is that whatever the angle or the position of the inner viewing zone relative to the outer rim of the eyepiece, said eyepiece can be set in either the left eye socket of the face piece of the protective device or, simply by reversing the eyepiece, in the right eye socket of the said face-piece. Another advantageous aspect of this eyepiece is that by varying the position of the inner viewing zone the wearing of spectacles may be accommodated within the protective device.

The eyepiece of this invention may be manufactured from any of the transparent materials, for example glass or plastics material, that are employed in this art. Preferably the eyepiece is moulded in plastic and laminated with glass on the outside of the inner viewing zone. The face-piece of the protective device may, for example, be manufactured from rubber or any other material preferred in this art.

The eyepiece of this invention will now be described by way of example only, with particular reference to the figures in which, FIG. 1 represents a perspective view of one embodiment of the eyepiece of this invention, and FIG. 2 represents a perspective view of a second embodiment.

Figure 1:
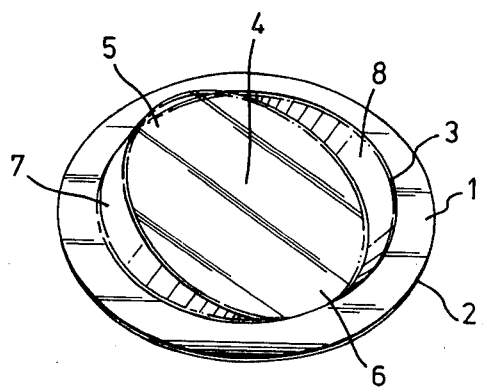

In FIG. 1 a unitary transparent eyepiece has an annular, planar outer rim 1 having a circular outer edge 2 and an inner edge 3. The circular planar inner viewing zone 4 has one half 5 extending in front of the plane of the outer rim 1 and one half 6 extending behind said plane. The upward extending portion 5 of the inner viewing zone 4 is joined to the inner edge 3 of the outer rim 1 by a crescent-shaped upward extending wall 7. The downward extending portion 6 of the inner viewing zone 4 is similarly joined to the inner edge 3 of the outer rim 1 by a crescent-shaped downward extending wall 8. The angle of the inner viewing zone 4 to the outer rim 1 is chosen so that when in position in the protective device the plane of the viewing zone 4 is orthogonal to the line of forward vision of the wearer.

Figure 2:
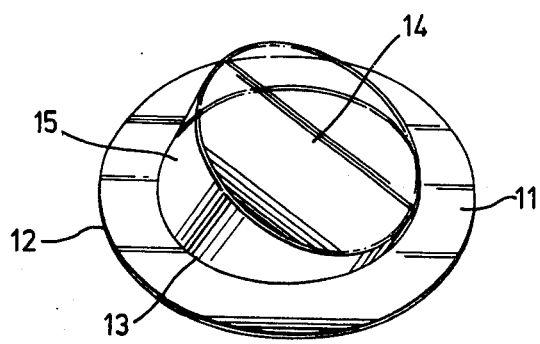

In FIG. 2 a further embodiment of a unitary transparent eyepiece has an annular, planar outer rim 11 with circular outer edge 12 and an inner edge 13. The circular planar inner viewing zone 14 is inclined to and extends out of the plane of the outer rim 11 and is joined to the inner edge 13 of said outer rim 11 by a single crescent-shaped upward extending wall 15 extending around substantially all of said edge 13. This eyepiece may be inserted into a protective device with the viewing zone extending either in front of or behind the plane of the outer rim depending on the design of the device.

Figure 3:
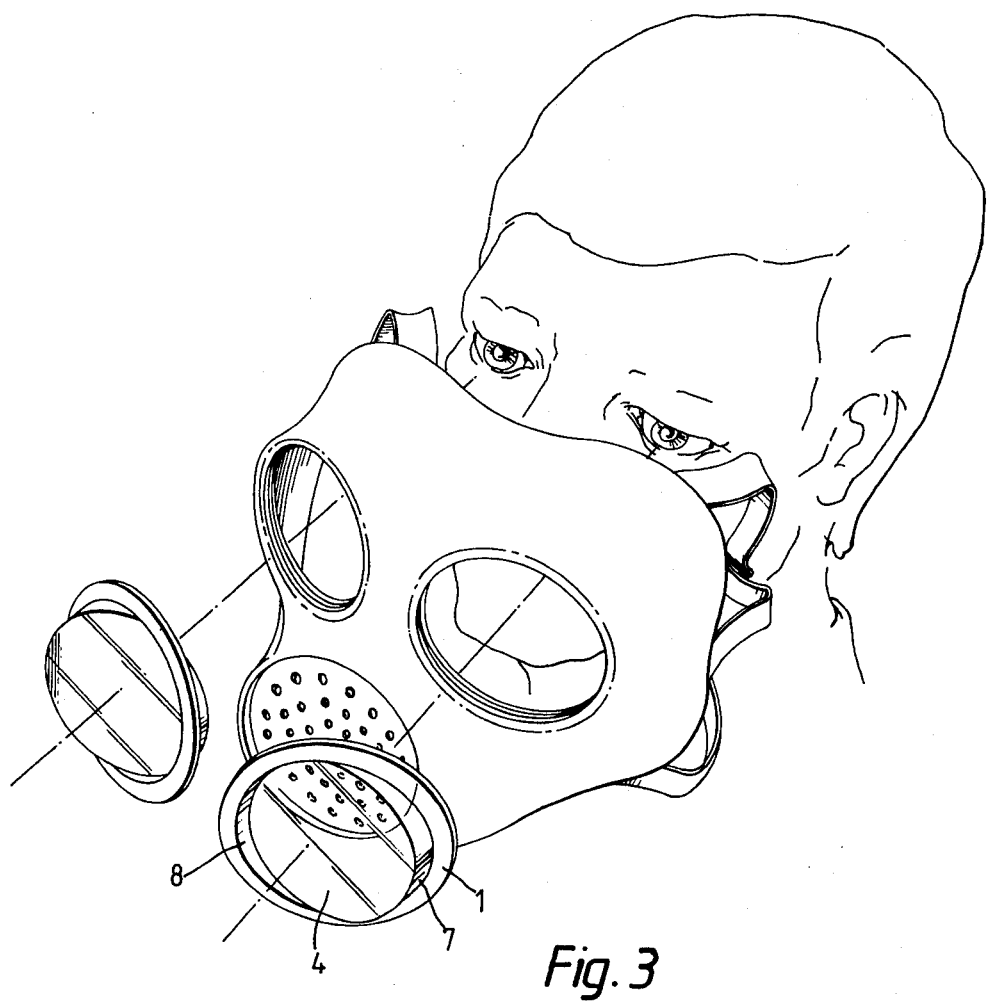
FIG. 3 represents an exploded perspective view of a face piece having two sockets, two eyepieces of the type represented in FIG. 1, and the position of the head of the wearer of the protective device in relation to the face piece.

In FIG. 3 two eyepieces of the type represented in FIG. 1 are shown in a disassembled relation to the complmentary planar sockets of the facepiece of a protective device. As can be seen in the drawing, when the eyepieces are in position in the sockets, the plane of the viewing zone 4 is orthogonal to the line of forward vision of the wearer of the protective device.

Figure 4:
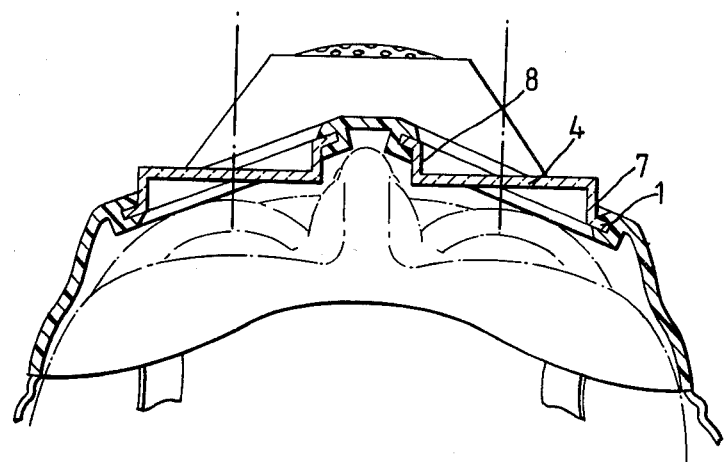
FIG. 4 represents a sectional view looking down onto the eyepieces and facepiece represented in FIG. 3, which are now shown in an assembled state. The view is taken along a plane passing horizontally through the center of each of the sockets of the face piece.

In FIG. 4 the eyepiece and facepiece represented in FIG. 3 are shown in an assembled state. As with FIG. 3, it is seen that when the eyepieces are fitted into the socket of the face piece, the plane of the viewing zone 4 is orthogonal to the line of forward vision of the wearer of the protective device. Also illustrated in FIG. 4 is the reception of the planar outer rim 1 of the eyepiece by the complementary planar socket of the facepiece.

I claim:

1. A unitary transparent eyepiece adapted to be fitted into a complementary left-eye or right-eye socket in a face piece, comprising a planar outer rim having an inner edge and a circular circumferential outer edge; and a planar inner viewing zone having a circular circumferential outer edge connected to the inner edge of the planar outer rim, the angle between the planes being such that, when the planar outer rim is fitted into either complementary socket of the face piece, the inner viewing zone of the eyepiece is orthogonal to the line of forward vision of a wearer of the face piece.

2. An eyepiece according to claim 1 formed from plastics material laminated with glass.

3. An eyepiece according to claim 1, wherein the plane of the outer rim bisects the inner viewing zone.

* * * * *